(12) United States Patent
DiFoggio

(10) Patent No.: US 7,408,645 B2
(45) Date of Patent: Aug. 5, 2008

(54) METHOD AND APPARATUS FOR A DOWNHOLE SPECTROMETER BASED ON TUNABLE OPTICAL FILTERS

(75) Inventor: Rocco DiFoggio, Houston, TX (US)

(73) Assignee: Baker Hughes Incorporated TX (US)

( * ) Notice: Subject to any disclaimer, the term of this patent is extended or adjusted under 35 U.S.C. 154(b) by 163 days.

(21) Appl. No.: 11/360,542

(22) Filed: Feb. 23, 2006

(65) Prior Publication Data

US 2006/0139646 A1  Jun. 29, 2006

Related U.S. Application Data

(63) Continuation-in-part of application No. 10/985,715, filed on Nov. 10, 2004.

(60) Provisional application No. 60/518,965, filed on Nov. 10, 2003.

(51) Int. Cl.
*E21B 47/00* (2006.01)
*G01N 33/28* (2006.01)
*G01N 21/59* (2006.01)

(52) U.S. Cl. .................. 356/436; 356/70; 250/256; 250/261; 175/40

(58) Field of Classification Search ............... 356/436
See application file for complete search history.

(56) References Cited

U.S. PATENT DOCUMENTS

| | | | | |
|---|---|---|---|---|
| 5,617,206 | A * | 4/1997 | Fay | 356/320 |
| 6,176,323 | B1 * | 1/2001 | Weirich et al. | 175/40 |
| 6,388,251 | B1 * | 5/2002 | Papanyan | 250/269.1 |
| 6,670,599 | B2 | 12/2003 | Wagner et al. | 250/214.1 |
| 6,879,014 | B2 | 4/2005 | Wagner et al. | 257/458 |
| 2002/0118459 | A1 | 8/2002 | Kuznetsov | |
| 2002/0175235 | A1 | 11/2002 | Swisher, Jr. et al. | 241/101.74 |
| 2003/0151818 | A1 | 8/2003 | Wagner et al. | 359/578 |

(Continued)

OTHER PUBLICATIONS

Yu, Bing, Gary Pickrell, and Anbo Wang, "Thermally Tunable Extrinsic Fabry-Perto Filter", Oct. 2004, IEE Photonics Technology Letters, vol. 16, No. 10, pp. 2296-2298.*

(Continued)

*Primary Examiner*—Layla G. Lauchman
*Assistant Examiner*—Rebecca C Slomski
(74) *Attorney, Agent, or Firm*—Cantor Colburn LLP

(57) ABSTRACT

Thermally tunable optical sensors are used in sampling tools for analysis of samples from a wellbore. The thermally tunable optical sensors generate a series passbands of wavelength emissions and detect attenuation in a signal thereof. The attenuation detected is processed and used to determine aspects of the samples. Analysis may be completed remotely (outside of the wellbore), within the wellbore (during drilling or otherwise), or as a part of another process such as fluid management, transport and refinement.

18 Claims, 11 Drawing Sheets

U.S. PATENT DOCUMENTS

| | | |
|---|---|---|
| 2003/0118459 A1 | 9/2003 | Yadlowsky et al. |
| 2004/0062945 A1 | 4/2004 | Domash et al. ............. 428/641 |
| 2004/0234198 A1 | 11/2004 | Wagner et al. ................ 385/27 |
| 2004/0255853 A1 | 12/2004 | Ma et al. ................. 118/338.1 |
| 2005/0030628 A1 | 2/2005 | Wagner et al. ........... 359/338.1 |
| 2005/0056773 A1 | 3/2005 | Kaneko |
| 2005/0074206 A1 | 4/2005 | Domash et al. .......... 385/338.1 |
| 2005/0082480 A1 | 4/2005 | Wagner et al. ........... 250/338.1 |
| 2005/0023440 A1 | 5/2005 | Matthews |
| 2005/0105184 A1 | 5/2005 | Ma et al. .................... 359/578 |
| 2005/0105185 A1 | 5/2005 | Mia et al. |
| 2005/0157392 A1 | 7/2005 | Choi et al. |
| 2005/0230601 A1 | 10/2005 | Tholl et al. |
| 2005/0264808 A1* | 12/2005 | Wang ........................ 356/328 |
| 2006/0056029 A1 | 3/2006 | Ye |

OTHER PUBLICATIONS

Domash, et al. "Tunable thin-film filters based on thermo-optic semiconductor films" Aegis Photonics N Jun. 2002. Aegis Semiconductor, Inc., Woburn, MA 01801 USA (11 pages).

Domash, Lawrence. "Tunable Thin Film Filters Using Thermo-Optic Silicon", Aegis-OSA-MOIC-Sep. 2004. (3 pages).

* cited by examiner

US 7,408,645 B2

METHOD AND APPARATUS FOR A DOWNHOLE SPECTROMETER BASED ON TUNABLE OPTICAL FILTERS

CROSS REFERENCE TO RELATED APPLICATIONS

This application is filed under 37 CFR 1.53(b) as a continuation-in-part of and claims priority under 35 U.S.C. 120 to U.S. patent application Ser. No. 10/985,715 filed on Nov. 10, 2004, which claims priority from U.S. Provisional Patent Application No. 60/518,965 filed on Nov. 10, 2003, these applications being incorporated by reference herein in their entirety.

BACKGROUND OF THE INVENTION

1. Field of the Invention

The present invention relates generally to the field of downhole sampling of hydrocarbons and in particular to downhole and onsite surface high resolution spectroscopy of hydrocarbon samples using a tunable optical filter for measurement and estimation of physical and chemical properties of fluid from a downhole formation.

2. Background Information

In the oil and gas industry, formation testing tools have been used for monitoring formation pressures along a wellbore, obtaining formation fluid samples from the wellbore and predicting performance of reservoirs around the wellbore. Such formation testing tools typically contain an elongated body having an elastomeric packer that is sealingly urged against the zone of interest in the wellbore to collect formation fluid samples in storage chambers placed in the tool.

During drilling of a wellbore, a drilling fluid ("mud") is used to facilitate the drilling process and to maintain a pressure in the wellbore greater than the fluid pressure in the formations surrounding the wellbore. This is particularly important when drilling into formations where the pressure is abnormally high. If the fluid pressure in the borehole drops below the formation pressure, there is a risk of blowout of the well. As a result of this pressure difference, the drilling fluid penetrates into or invades the formations for varying radial depths (referred to generally as invaded zones) depending upon the types of formation and drilling fluid used. The formation testing tools retrieve formation fluids from the desired formations or zones of interest, test the retrieved fluids to ensure that the retrieved fluid is substantially free of mud filtrates, and collect such fluids in one or more chambers associated with the tool. The collected fluids are brought to the surface and analyzed to determine properties of such fluids and to determine the condition of the zones or formations from where such fluids have been collected.

One feature that most formation testing tools have in common is a fluid sampling probe. This may consist of a durable rubber pad that is mechanically pressed against the rock formation adjacent the borehole, the pad being pressed hard enough to form a hydraulic seal. Through the pad is extended one end of a metal tube that also makes contact with the formation. This tube ("probe") is connected to a sample chamber that, in turn, is connected to a pump that operates to lower the pressure at the attached probe. When the pressure in the probe is lowered below the pressure of the formation fluids, the formation fluids are drawn through the probe into the well bore to flush the invaded fluids prior to sampling. In some formation tests, a fluid identification sensor determines when the fluid from the probe consists substantially of formation fluids; then a system of valves, tubes, sample chambers, and pumps makes it possible to recover one or more fluid samples that can be retrieved and analyzed when the sampling device is recovered from the borehole.

It is desirable that only uncontaminated fluids are collected, in the same condition in which they exist in the formations. Commonly, the retrieved fluids are contaminated by drilling fluids. This may happen as a result of a poor seal between the sampling pad and the borehole wall, allowing borehole fluid to seep into the probe. The mud cake formed by the drilling fluids may allow some mud filtrate to continue to invade and seep around the pad. Even when there is an effective seal, borehole fluid (or some components of the borehole fluid) may "invade" the formation, particularly if it is a porous formation, and be drawn into the sampling probe along with connate formation fluids.

U.S. Pat. No. 4,994,671 issued to Safinya et al. discloses a device in which visible and near infrared (IR) analysis of the fluids is done in the borehole, primarily for the purpose of determining when a fluid being pumped has reached its minimum filtrate contamination and is worth collecting into a sample tank, which will be subsequently be brought back to the surface. The infrared portion part of the electromagnetic spectrum (0.8 to 25 μm wavelength region, or equivalently wavenumbers of 12,500 to 400 $cm^{-1}$) of a substance contains absorption features due to the molecular vibrations or rotations of the constituent molecules. The absorptions arise from both fundamentals (single quantum transitions occurring in the mid-infrared region from 2.5-25.0 microns) and combination bands and overtones (multiple quanta transitions occurring in the mid- and the near-infrared region from 0.8-2.5 microns). The position (frequency or wavelength) of these absorptions contain information as to the types of molecular structures that are present in the material, and the intensity of the absorptions contains information about the amounts of the molecular types that are present. To use the information in the spectra for the purpose of identifying and quantifying either components or properties requires that a calibration be performed to establish the relationship between the absorbances and the component or property that is to be estimated. For complex mixtures, where considerable overlap between the absorptions of individual constituents occurs, such calibrations must be accomplished using various chemometric data analysis methods.

In complex mixtures, each constituent in the retrieved fluid generally gives rise to multiple absorption features corresponding to different vibrational motions. To first order, the effect on the mixture spectra of any interactions (e.g., hydrogen bonding) between the molecules of different components are negligible so that Beer's Law is obeyed and the intensities of these absorptions will all vary together in a linear fashion as the concentration of the constituent varies. Such features are said to have intensities which are correlated in the frequency (or wavelength) domain. This correlation allows these absorptions to be mathematically distinguished from unrelated spectral features and from random spectral measurement noise which shows no such correlation. The linear algebra computations which separate the correlated absorbance signals from the uncorrelated ones form the basis for techniques such as Multiple Linear Regression (MLR), Principal Components Regression (PCR) and Partial Least Squares (PLS). As is well known, PCR is essentially the analytical mathematical procedure of Principal Components Analysis (PCA) followed by regression analysis.

PCR and PLS have been used to estimate elemental and chemical compositions and to a lesser extent physical or thermodynamic properties of solids, liquids and gases based on their mid- or near-infrared spectra. Some examples of using chemometrics to infer physical and chemical properties of crude oils from their near-infrared spectra were given in 1988 in GB 2,217,838A where the spectra were obtained in the laboratory using a high-resolution (2-nm step size) spectrometer. Typically, chemometric methods involve: [1] the collection of mid-infrared or near-infrared spectra of a set of representative samples; [2] mathematical treatment of the spectral data to extract the best correlating individual wavelengths (MLR), or Principal Components or Partial Least Squares latent variables (e.g. the correlated absorbance signals described above); and [39 regression of these spectral variables against composition and/or property data to build a multivariate model. The analysis of new samples then involves the collection of their spectra, the decomposition of the spectra in terms of the spectral variables used in the regression and the application of the regression equation to calculate the composition or properties.

In Safinya et al., visible and near-infrared light is passed through the fluid sample. Then, a spectrometer (which is actually a filter photometer that has 10 filters at different center wavelengths) measures the spectrum of the transmitted and the back scattered light, and, knowing the spectrum of the incident light, transmission and backscattered absorption spectra for the sample are determined. Using absorption spectra of water, and particular examples of absorption spectra of gas, crude and refined oils, and drilling fluids, a least squares analysis is performed that models the observed spectra as a weighted sum of the spectra of its components, the least squares analysis giving the composition of the fluid in terms of weights of the various components. The Safinya method assumes that the spectra of the crude oil and of the filtrate that comprise a contaminated formation fluid mixture are the same as whatever example crude oil and filtrate spectra were chosen for the least-squares fitting. However, when testing any hydrocarbon-bearing zone for the first time, that assumption is problematic because of the high variability of crude oil spectra.

Currently, typical downhole spectrometers are actually filter photometers. They use fixed, single-color interference filters whose bandpass resolution is limited to no better than 11 nm full width at half maximum because of the present state of the art for manufacturing interference-filters, thus providing relatively low spectroscopic resolution at a small number of selected center wavelengths (e.g., 10 to 24 different optical filters). These filters are not suitable to distinguish between closely spaced spectral peaks or to identity isotopes whose spectral peak spacings are much smaller than 11 nm. Thus, there is a need for an analysis technique suitable for downhole and onsite surface spectroscopic analysis of hydrocarbon samples with higher resolution.

SUMMARY OF THE INVENTION

Disclosed is a sampling tool for providing spectroscopic data for a sample from a wellbore, the tool having sampling apparatus for collecting the sample and disposing at least a portion of the sample within a sample chamber; the sample chamber including at least one thermally tunable optical sensor for interrogating the sample and providing sample analysis data to a controller, the controller producing from the sample analysis data the spectroscopic data for the sample.

Also disclosed is a method for providing spectroscopic data for a sample from a wellbore, the method including collecting the sample from the wellbore; disposing at least a portion of the sample within a sample chamber, the sample chamber having at least one thermally tunable optical sensor for interrogating the sample and providing sample analysis data to a controller; illuminating the sample with a series of passbands of wavelength emissions; detecting the series to produce a detection signal; providing the detection signal to a processor; and, processing the detection signal to provide the spectroscopy data.

Further disclosed is a computer program product stored on machine readable media and having instructions for providing spectroscopic data for a sample from a wellbore, the instructions for collecting the sample from the wellbore; disposing at least a portion of the sample within a sample chamber, the sample chamber having at least one thermally tunable optical sensor for interrogating the sample and providing sample analysis data to a controller; illuminating the sample with a series of passbands of wavelength emissions; detecting the series to produce a detection signal; providing the detection signal to a processor; and, processing the detection signal to provide the spectroscopy data.

Examples of certain features of the invention have been summarized here rather broadly in order that the detailed description thereof that follows may be better understood and in order that the contributions they represent to the art may be appreciated. There are, of course, additional features of the invention that will be described hereinafter and which will form the subject of the claims appended hereto.

BRIEF DESCRIPTION OF THE FIGURES

For detailed understanding of the present invention, references should be made to the following Detailed Description of the Invention, taken in conjunction with the accompanying drawings, in which like elements have been given like numerals, wherein.

DETAILED DESCRIPTION OF THE INVENTION

The teachings herein provide for high-resolution spectroscopy (HRS) by making use of at least one thermally tunable optical sensor selected from various embodiments. Examples of tunable optical sensors include thermally tunable optical sensors, Fabry-Perot, Complaint Micro Electromechanical System, and others. The sensors are used to estimate, determine, or quantify a variety of aspects of samples taken from formation fluid. The estimations, determinations and quantifications are achieved through collection of spectra and spectral analysis. The collection may be undertaken or completed within the wellbore 11 or "topside" as may be desired.

As disclosed herein, one embodiment of the sensor that offers certain advantages over other embodiments is that of the thermally tunable optical sensor. Accordingly, the disclosure herein generally refers to thermally tunable optical sensors and embodiments thereof. However, it should be recognized that the use of thermally tunable optical sensors is not limiting of the teachings herein. For example, in some embodiments, reference to the thermally tunable optical sensor may actually contemplate and encompass a plurality of thermally tunable optical sensors. In other embodiments, the thermally tunable optical sensor may be used in conjunction with other sensors, such as the Fabry-Perot filter.

One non-limiting example of a thermally tunable optical filter is disclosed in the U.S. Patent Application Publication No.: US/2005/0030628 A1, entitled "Very Low Cost Narrow Band Infrared Sensor," published Feb. 10, 2005, the disclosure of which is incorporated by reference herein in its entirety.

Figure 1:
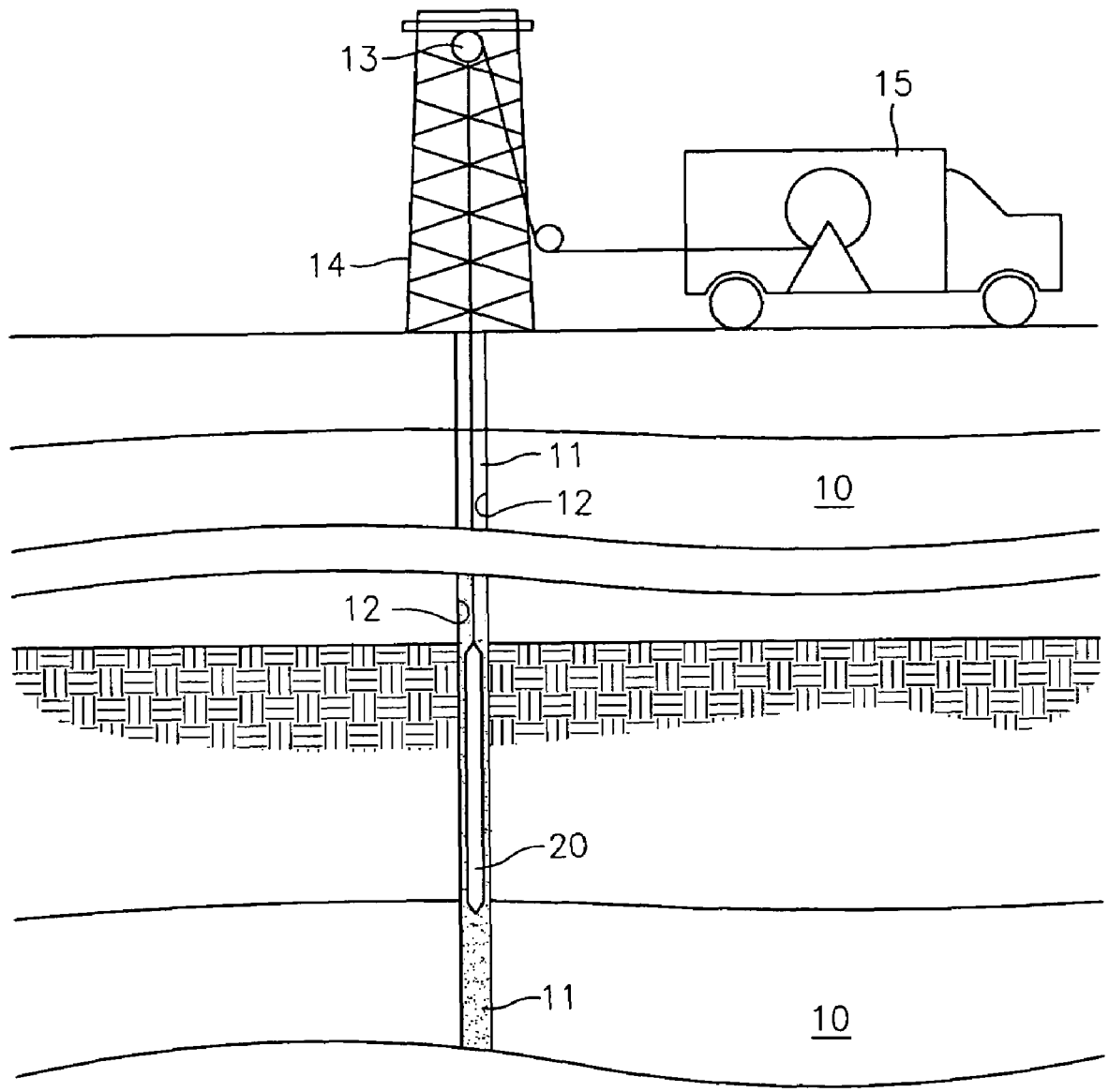
FIG. 1 depicts aspects of sampling in a wellbore with a sampling tool.

Turning now to FIG. 1, a cross-section of earth 10 along the length of a penetration referred to as a "wellbore" 11 is depicted. Usually, the wellbore 11 is at least partially filled with a mixture of liquids including water, drilling fluid, and formation fluids that are indigenous to the earth formations penetrated by the wellbore 11. Suspended within the wellbore 11 at the bottom end of a wireline 12 is a formation fluid sampling tool 20. The wireline 12 is often carried over a pulley 13 supported by a derrick 14. Wireline 12 deployment and retrieval is typically performed by a powered winch carried by a service truck 15.

Figure 2:
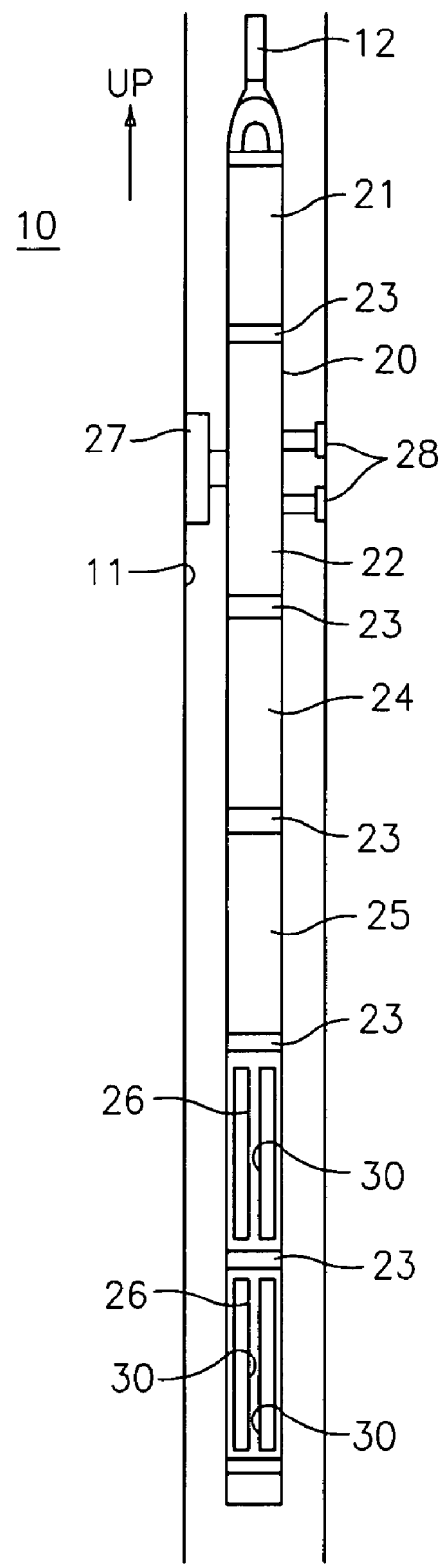
FIG. 2 depicts aspects of the sampling tool.

An exemplary embodiment of the sampling tool 20 is schematically illustrated by FIG. 2. The sampling tool 20 may include an assembly of several tool segments that are joined end-to-end by the threaded sleeves or mutual compression unions 23. The assembly of tool segments appropriate for the present invention may include a hydraulic power unit 21 and a formation fluid extractor 22. Below the extractor 22, a large volume pump 24 is provided for line purging. Below the large volume pump 24 is a similar small volume pump 25 having a smaller displacement volume that is quantitatively monitored. Ordinarily, one or more sample tank module sections 26 are assembled below the small volume pump 25. Each module section 26 typically includes at least one fluid sample tank 30.

In this embodiment, the formation fluid extractor 22 includes an extensible suction probe 27 that is opposed by backup arms 28. Both, the suction probe 27 and the opposing backup arms 28 are hydraulically extensible to firmly engage the walls of the wellbore 11. Construction and operational details of the sampling tool 20 are well known in the art. Accordingly, further discussion of aspects the sampling tool 20 is generally omitted herein.

Figure 3:
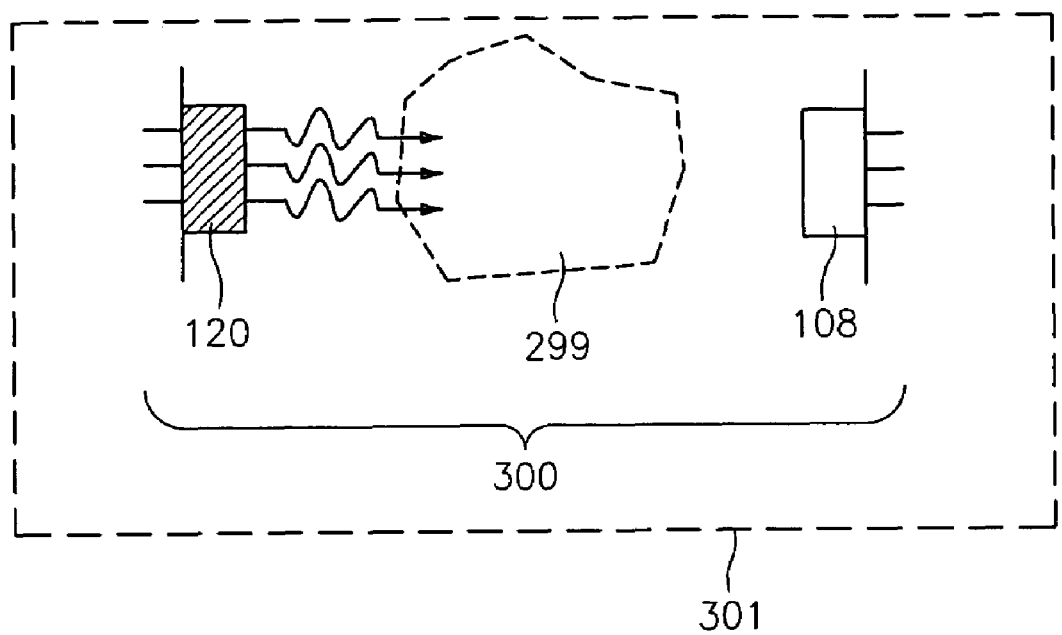
FIG. 3 depicts a sample chamber.

Aspects of the sample chamber are depicted in FIG. 3. Typically, within the sampling tool 20 is a sample chamber 301. In non-limiting embodiments presented herein, a sample 299 is disposed within the sample chamber 301. The sample 299 is illuminated by the thermally tunable optical sensor 300. In FIG. 3, the thermally tunable optical sensor 300 typically includes a tunable optical emitter 120 and a detector 108, however aspects of the thermally tunable optical sensor 300 discussed in greater detail below. As an overview, the tunable optical emitter 120 produces some bandwidth of infrared (IR) light whose center-wavelength is adjustable and is detected by the detector 108 after passing through a sample 299 (that is, a spectrometer based on the pre-filtering of light). The wavelengths of IR traverse the sample 299. Tuning of the thermally tunable optical sensor 300 provides interrogation of the sample 299 to determine the presence and other aspects of a constituent of interest in the sample 299. Alternatively, a beam of white light can first pass through the sample 299 and then only some portion of the transmitted light will pass through the thermally tunable filter and onto the detector 108 (that is, a spectrometer based on the post-filtering of light).

The thermally tunable optical sensor 300 is coupled to equipment as is typically used for signal processing. Exemplary equipment include, without limitation, a processor, a power supply, a memory, a storage, an input device and an output device. As signal processing equipment is known in the art, and not a part of this invention per se, further discussion of such equipment is generally omitted herein.

Although disclosed herein in terms of having infrared emissions and operating in the infrared region, it is recognized that the thermally tunable optical sensor 300 may operate at other wavelengths. For example, the thermally tunable optical sensor 300 may operate in the near infrared region. In fact, although the present embodiments refer to operation in the infrared (IR) region, the teachings herein could make use of any wavelength emission, where a constituent of interest within a sample has an absorption band. Therefore, the use of IR herein is merely illustrative of aspects of the invention, and not limiting thereof.

Further, as used herein, "constituent of interest" generally makes reference to a chemical component of the sample 299. The constituent of interest is typically the chemical component for which the thermally tunable optical sensor 300 has been selected. For example, in one embodiment, carbon monoxide (CO) is the constituent of interest. In this embodiment, CO has a principle absorption band at about 4.7 µm. As the thermally tunable optical sensor 300 has a finite useful optical operating range, the thermally tunable optical sensor 300 is selected to have the optical operating range centered about an absorption band for CO, or at about 4.7 µm. Aspects of this relationship are depicted in greater detail in FIG. 4.

Figure 4:
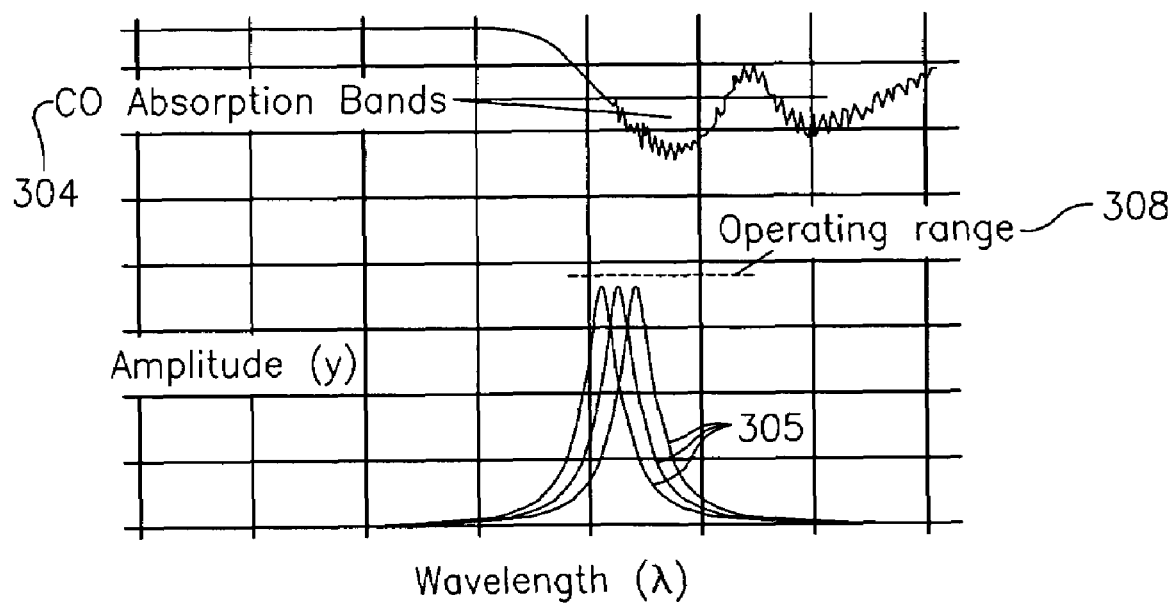
FIG. 4 provides an overview of microtuning a thermally tunable optical sensor.

In FIG. 4, a series of different passband emissions 305 are shown. The series of passband emissions 305 depicted is indicative of at least a portion of the thermally tunable optical sensor 300 optical operating range 308. Generation of the series of passband emissions 305 occurs in the emitter 120 through a process referred to herein as "microtuning," and may also be referred to as "sweeping" over the optical operating range 308. The thermally tunable optical sensor 300 is typically tuned by filtering a broad band emission with a filter to selectively pass a first passband emission centered about a first wavelength, and then tuning the filtering of the broad band emission to selectively pass a second passband emission centered about an incrementally greater (or lower) second wavelength. Accordingly, the thermally tunable optical sensor 300 may be tuned over the optical operating range 308. Absorption bands 304 of the constituent of interest absorb at least a portion of at least one correlating passband of emissions within the series of passband emissions 305. Accordingly, the detector 108, which detects a signal for the passband of emissions, passes signal information to a processor. The processor employs known signal processing techniques to determine the significance of any changes such as attenuation (referred to as "dips") in the signal. The significance may be correlated to aspects such as, without limitation, chemical identity and concentration.

Accordingly, one skilled in the art will understand that a plurality of thermally tunable optical sensors 300 may be employed to provide comprehensive spectral analysis for the sample 299. That is, each of the plurality may be selected to analyze specific aspects of the sample 299. In this embodiment, the processor provides for aggregation of sample data and provision of the comprehensive spectral analysis data.

Although the teachings herein provide for a high-resolution spectrometer using a thermally tunable optical sensor 300, it is considered that the term "high-resolution" may be, in at least some instances, a subjective term. For purposes of the present disclosure, high-resolution spectrometry generally refers to resolution of typically better than 100 nanometers for a mid-infrared region of the electromagnetic spectrum, and typically better than 10 nanometers for a near infrared region. This general rule is, however, not limiting of the teachings. For example, in practical terms for the disclosure herein, the term "high-resolution" may refer to spectroscopy performance that provides for adequate separation and resolution of constituents of interest. Accordingly, while one skilled in the art may consider that less than 100 nanometers is desirable, such performance may not always be required. For example, in some instances the signal derived from interrogating a constituent of interest may be greatly separated from other commonly occurring constituents of interest. In these instances, it may not be necessary to include resolution within an arbitrarily selected bandwidth that might be desired for other assessments.

Further, and in keeping with considerations of resolution, the term "passband" is not to be limiting of the teachings herein. That is, "passband," as used herein, generally provides for distinction between bands of wavelengths generated during the microtuning of the thermally tunable optical sensor 300. In practice, passbands of wavelengths may not be very narrow, particularly when taken in the context of other applications not relevant to these teachings. Suffice to say, that the series of passbands of (wavelength) emissions 305 provides for adequate distinctions (within the series) and lends support to spectroscopy at an acceptable level of performance. In practice, the actual full width half maximum of the passband of wavelengths will depend on a variety of constraints, such as the construction and operating conditions (e.g., temperature) for the thermally tunable optical sensor 300.

Accordingly, one skilled in the art will understand that the use of at least one thermally tunable optical sensor 300 can provide for determinations regarding at least one constituent of interest in the sample 299. Typically, a plurality of thermally tunable optical sensors 300 is included in an instrument for analysis of the sample 299. In these embodiments, each thermally tunable optical sensor 300 of the plurality has an operating range 308 centered about and is microtuned about certain wavelengths of interest, the wavelengths of interest correlating to known absorption bands for a constituent. In this manner, the constituents of a relatively homogeneous sample 299 may be determined.

Turning now in more detail to the thermally tunable optical sensor 300, one of the primary examples for illustration of operation of the thermally tunable optical sensor 300 a CO gas sensor that uses a tunable optical emitter 120 (TOE) to direct narrow band infrared (IR) light through a gas sample and onto a detector 108. The thermally tunable optical sensor 300 generally modulates the wavelength of the IR light back and forth across the CO spectral absorption features, i.e., from about 4500 nm to about 4700 nm.

Figure 5:
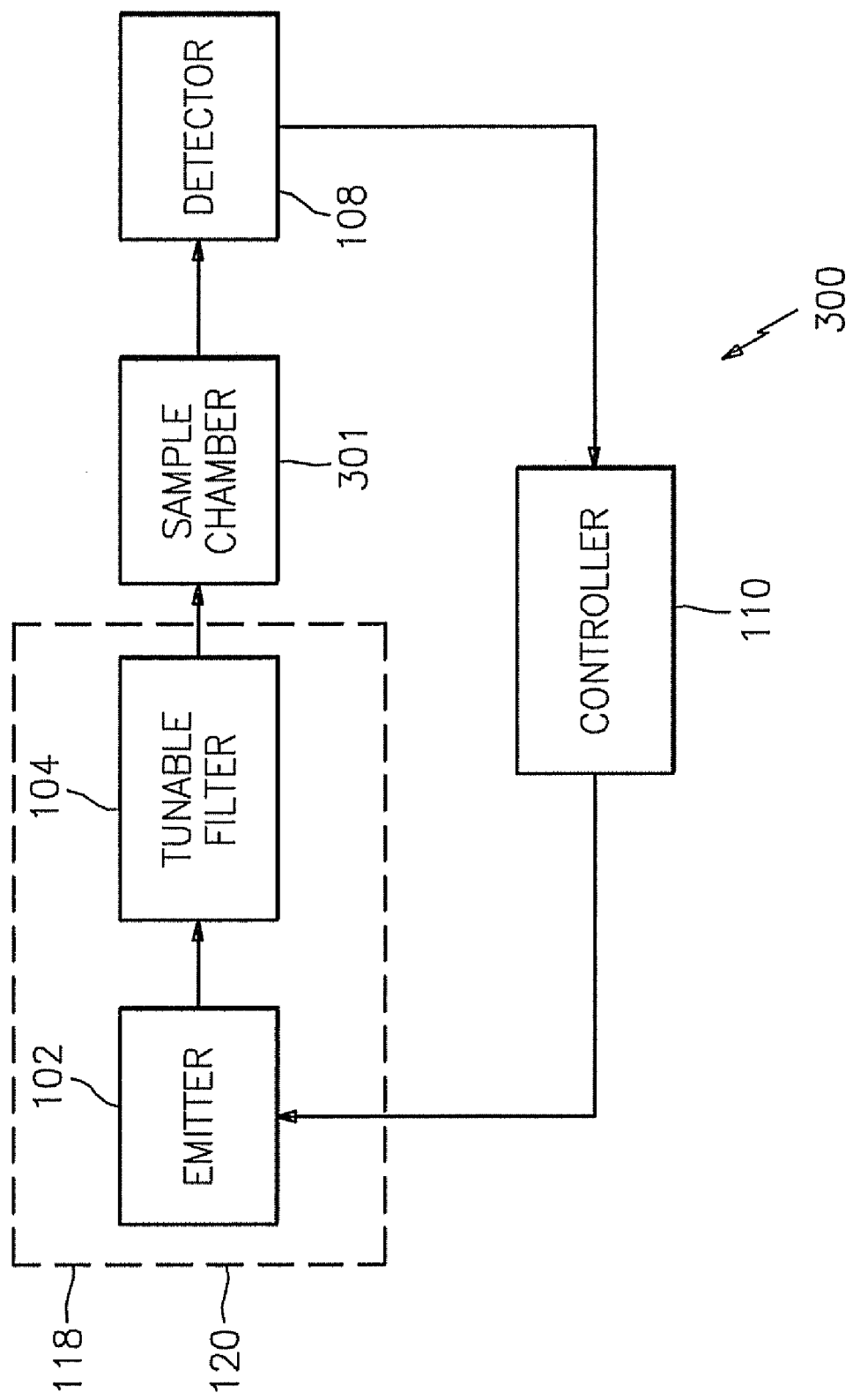
FIG. 5 is a block diagram depicting components of the thermally tunable optical sensor.

As is described in more detail below, the TOE 120 includes a blackbody emitter that is associated with the thermally tunable optical sensor 300, either by proximity with little or no thermal coupling, or by direct integration so that the emitter and filter are thermally coupled. In FIG. 5, the broken-lined box 118 represents an association between an emitter 102 and a tunable optical filter 104, so as to form the tunable optical emitter 120 (TOE). Typically, the TOE 120 is realized in one of two main embodiments.

In a first embodiment of the TOE 120, a fixed emitter with a constant output spectrum and magnitude provides back-illumination to the tunable optical filter 104. The emitter 102 and tunable optical filter 104 may be arranged in a single package, such as a can or other suitable electronics package known in the art. The tunable optical filter 104 typically includes a heating mechanism (e.g., a resistor) for tuning, wherein the heating mechanism is independent of the emitter 102. The emitter 102 is typically at a constant, relatively high temperature (for example, between about 500° C. to about 10,000° C.) to provide intense emission. In contrast, the temperature of the tunable optical filter 104 is typically much lower, and varies over a range of temperatures (for example, from about 25° C. to about 4000° C.). The varying provides for the tuning. A wavelength-to-temperature tuning rate of 0.6 nm/° C. is typical for germanium materials and mid-IR design. Typically, wavelength-to-temperature tuning rates are about 1.3E-04 of the center wavelength/° C. for germanium, and 6E-05 of center wavelength/° C. for silicon.

In the case of the emitter 102 mounted in proximity to the tunable optical filter 104 having the independent heating mechanism incorporated therein, the emitter 102 is usually at least somewhat thermally isolated from the tunable optical filter 104, to avoid aberrations in tuning. Thermal separation can be achieved through a variety of techniques, including providing a sufficient distance between the elements and by proper packaging.

Figure 6A:
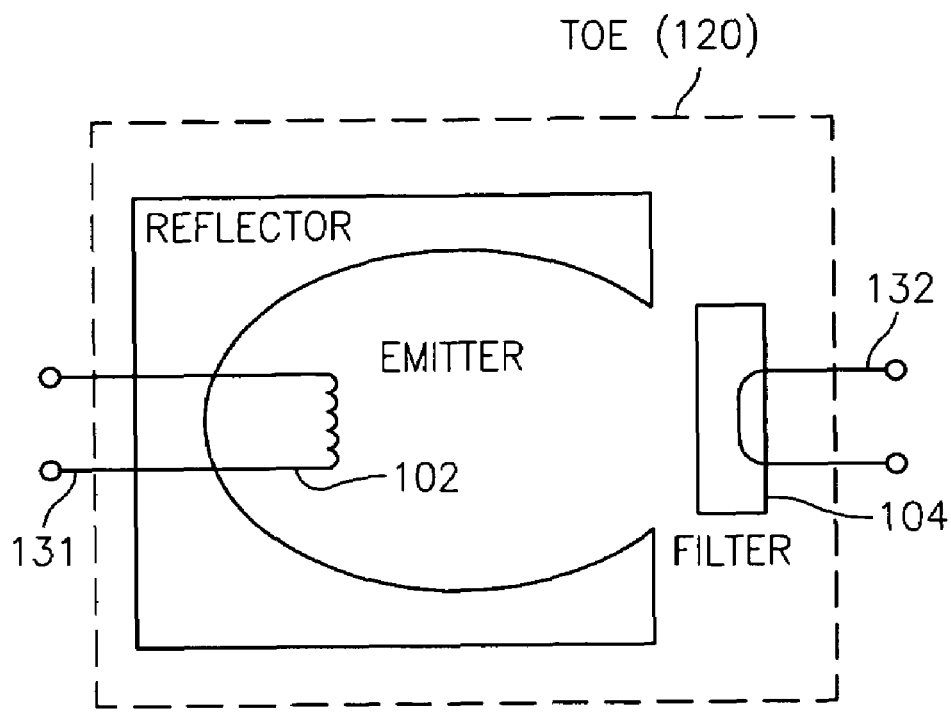
FIG. 6A and FIG. 6B, collectively referred to as FIG. 6, depict aspects of one embodiment of a tunable optical emitter.
Figure 6B:
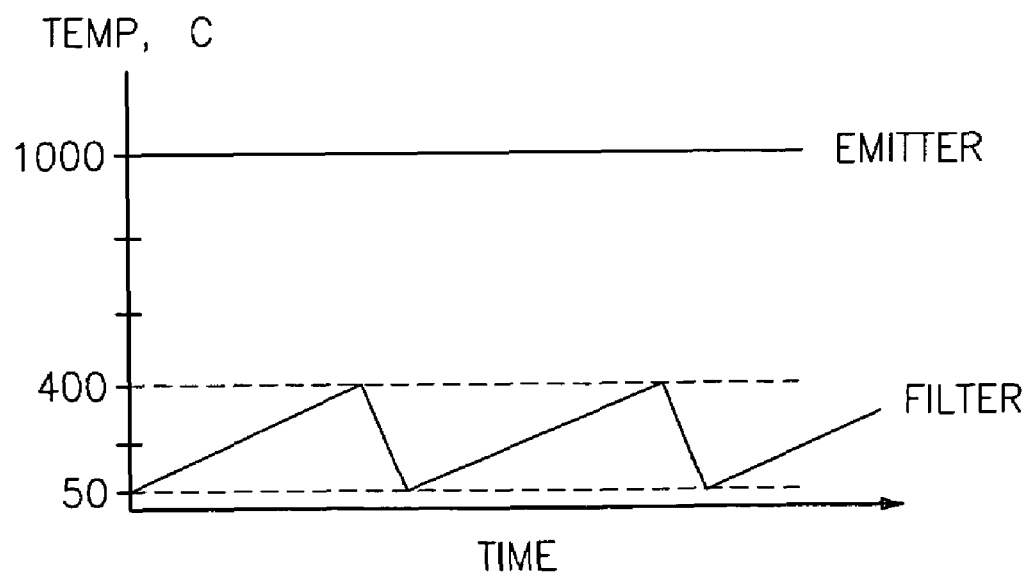

As shown in FIG. 6A, providing a metal parabolic, elliptical or other shaped back-reflector 60 to concentrate the IR emission and guide it to an aperture of the tunable optical filter 104 typically improves the efficiency of the emitter 102. An elliptical reflector 60, as shown in FIG. 6A, may be used to refocus light from the emitter 102 to the input aperture of the tunable optical filter 104. FIG. 6B shows that during the scanning process, the temperature of the emitter 102 stays substantially constant by use of a first heating circuit 131. In contrast, the temperature of the tunable optical filter 104 is periodically cycled by use of an independent second heating circuit 132.

Figure 7A:
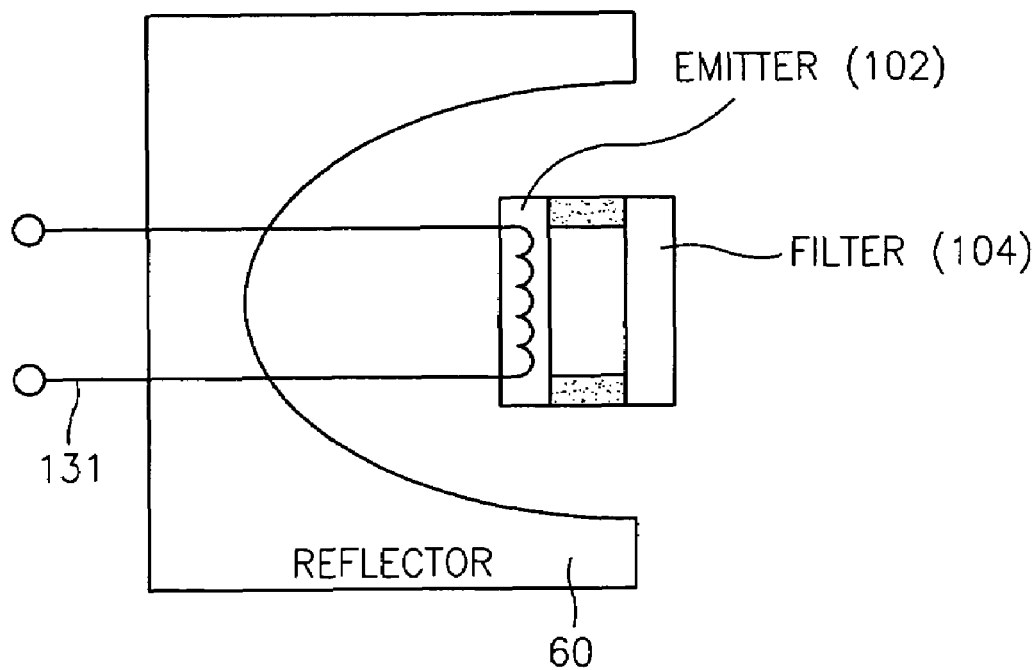
FIG. 7A and FIG. 7B, collectively referred to as FIG. 7, depict aspects of one embodiment of another tunable optical emitter.

Depicted in FIG. 7A is a second embodiment of the TOE 120, referred to herein as the Integrated TOE 121 (ITOE), includes a thermal coupling with an IR emitter, either through minimal separation, or by directly attaching the tunable optical filter 104 to the emitter 102, such as by use of a bonding material or other securing technique. As with the first embodiment of the TOE 120, the emitter 102 and tunable optical filter 104 of the ITOE 121 may also be arranged in a single package, such as a can or other suitable electronics package known in the art. Typically, the reflector 60 is parabolic and included with the ITOE 121 to direct emissions. The thermal coupling causes the tunable optical filter 104 to be heated (hence, tuned) directly by the emitter 102. Accordingly, the tunable optical filter 104 does not need an internal or independent heating mechanism. Although the thermal coupling may include at least one of radiative coupling and conductive coupling, radiative coupling is typically employed as radiative coupling allows a greater change in temperature with respect to time.

Figure 7B:
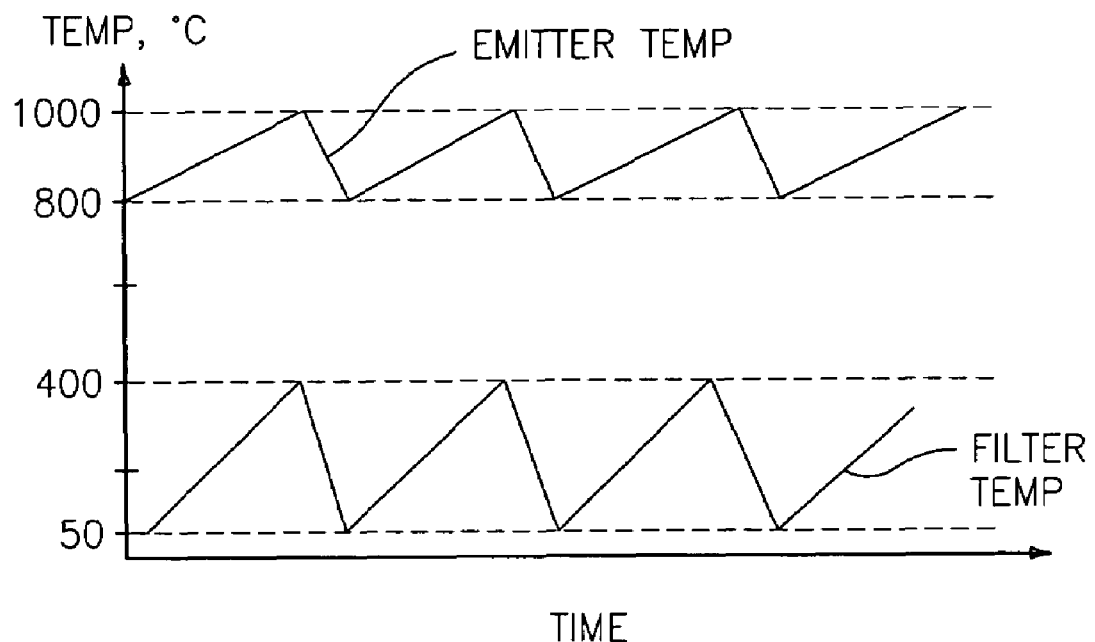

In this embodiment, the temperature of the emitter 102 is periodically varied instead of operating at a constant temperature. The range of temperature is typically between about 800° C. and about 1000° C. This typically causes the tunable optical filter 104 to be heated through the thermal coupling between about 100° C. and about 400° C. An exemplary heating profile for this relationship is depicted in FIG. 7B. The relationship between the temperature range of the emitter 102 and the temperature range of the tunable optical filter 104 is arranged by proper structure and dimensioning, and by providing the tunable optical filter 104 with suitable layers that absorb wavelengths the tunable optical filter 104 does not transmit, thereby enhancing the coupling to the emitter 102.

Other versions of this embodiment may use different temperature ranges and relationships. Advantageously only one heating mechanism is used for the emitter 102. Thus, a fully integrated tunable optical emitter 121 can be fabricated to a very small scale.

Figure 8:
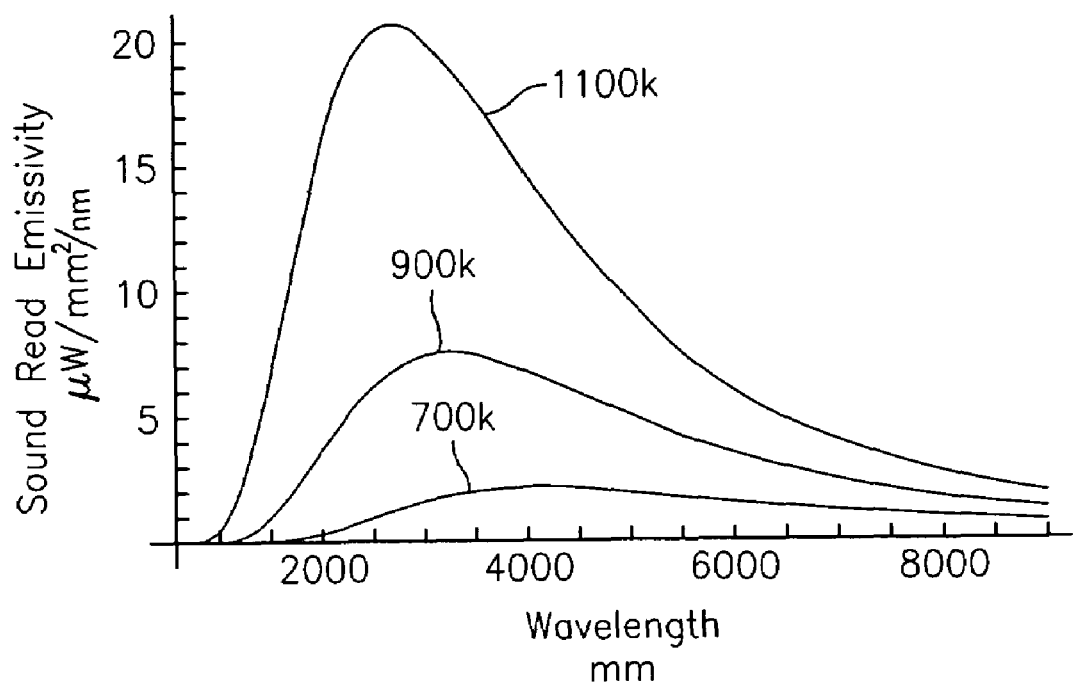
FIG. 8 depicts emissions versus wavelength.
Figure 9:
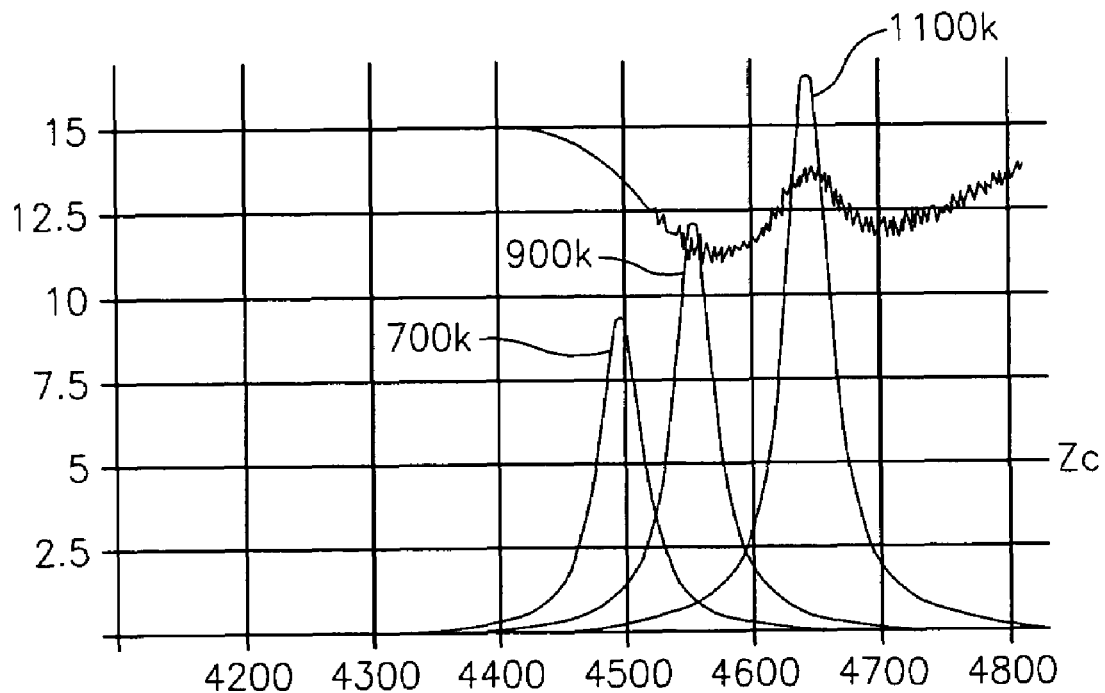
FIG. 9 depicts various tuning states for the thermally tunable optical sensor.
Figure 10:
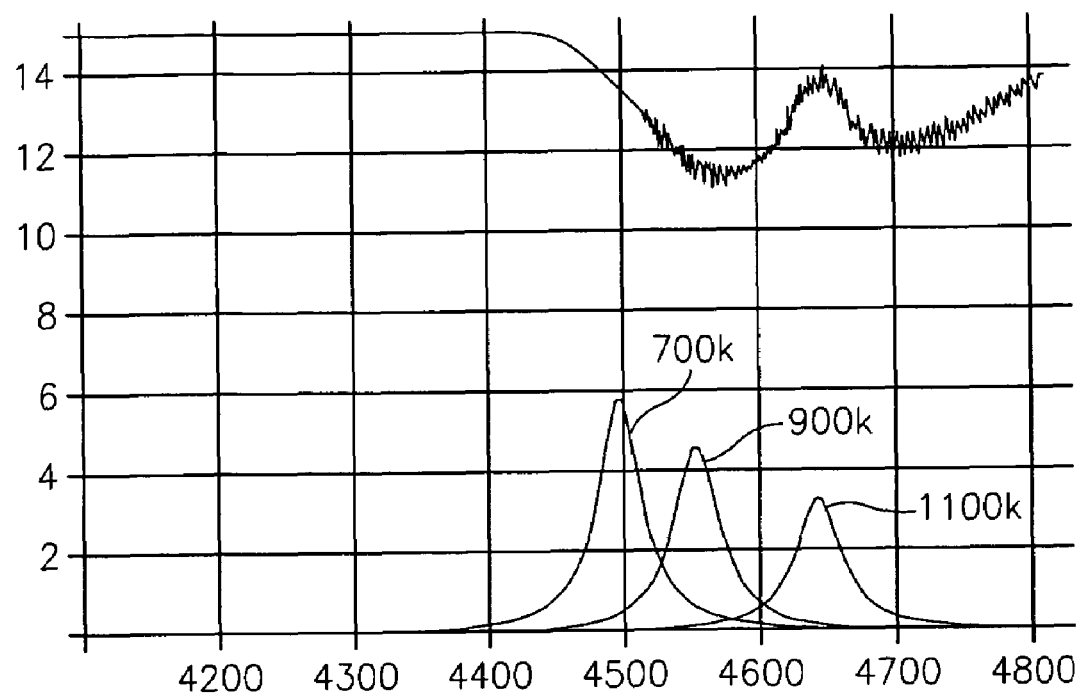
FIG. 10 depicts the various tuning states of FIG. 9, accounting for a filter.

It is well known that as the temperature of a blackbody emitter increases, the emission at any given wavelength will rise as well, as shown in FIG. 8. One might therefore expect that the output of the ITOE 121 would also increase as tuning proceeds (aspects of which are shown in FIG. 9). Such variations in output power are generally undesirable, especially if the variations are excessive. However, as the transmissivity of germanium decreases as its temperature increases, for tunable optical filters 104 that use germanium films, the decrease in transmissivity tends to offset the increased blackbody illumination as the emitter 102 heats (and hence tunes) the tunable optical filter 104, resulting in constant or substantially constant output intensity, as shown in FIG. 10. Notably, the tunable optical filter 104 is also a blackbody emitter, which further contributes to the overall intensity increase with respect to temperature. These factors may be combined to produce a TOE 120 with constant or nearly constant output intensity as the TOE 120 scans through the desired wavelengths. Small output variations can be compensated at or after the detector 108 via electronic techniques known in the art.

The CO gas sensor tunes at least one of the TOE 120 and ITOE 121 using a thermal mechanism, taking advantage of the inherent thermo-optic properties. The TOE 120 and the ITOE 121 are relatively inexpensive to fabricate by known techniques for thin film deposition, such as e-beam deposition, sputtering, and plasma enhanced chemical vapor deposition (PECVD). Further, relatively simple design variations may be realized to provide a wide range of bandwidths. Incorporating a TOE in a chemical sensor is therefore a low cost and volume-manufacturable approach to IR tunable filters and can be applied over a broad range of target wavelengths.

Referring back to FIG. 5, one embodiment a CO gas sensor 100 includes a blackbody emitter 102, a tunable optical filter 104, a sample chamber 301, a detector 108 and a controller 110. The blackbody emitter 102 provides broddband, blackbody radiation to the tunable optical filter 104. The controller 110 causes the tunable filter 104 to scan its transmission across a range of wavelengths corresponding to the CO absorption profile. The tunable optical filter 104 filters the light from the emitter 102 so as to produce filtered light with a spectrum that also scans across the same range of wavelengths. The filtered light from the tunable filter 104 enters the multipath gas cell 106, which is designed-to allow the filtered light to pass numerous times through the gas sample within the sample chamber 301. The detector 108 receives light from the sample chamber 301 after the light has passed through the sample 299, and produces a detection signal corresponding to the light received. The controller 110 analyzes the detection signal to determine if an absorption peak is present.

Various alternative emitter structures may be selected for long life, low cost, and intense IR output. Typically, the smallest possible emitter 102 is desired in order to provide for efficient operation. Such emitters 102 include conductively doped silicon chips, thin silicon membranes, thin membranes of diamond like carbon, or coils or filaments of metal (as used herein, a "membrane" may include a single thin film layer, or it may include multiple thin film layers stacked upon one another). Alloys of Cr with Ni, Fe, or Al (such as "nichrome" or "kanthal") are good choices for the metal coil or filament emitter, because they can operate in air at 1000° C. or more with long life, without requiring windows which would otherwise block IR emission between about 4000 nm to about 5000 nm.

The blackbody emitter 102 may include a silicon surface that is textured with micron-level features, resulting in a somewhat narrower blackbody spectrum as compared to a simple silicon film. The narrower blackbody spectrum allows a more efficient use of the power supplied to the emitter, since less out-of-band IR energy is wasted.

The tunable optical filter 104 may be a thermo-optic filter that provides a bandpass transmission response in the absorption feature range. In general, the tunable optical filters 104 described herein are bandpass filters that were developed for the telecommunications industry and for applications at or near 1500 nm. As is known, these filters can be single or multi-cavity, Fabry-Perot line-shape or flat top line-shape, and can operate at various bandwidths. Such filters are tunable by heating or cooling with internal conductive films or metal resistor films. The embodiments described herein extend this technology, primarily developed for use at 1.5 micron and using amorphous silicon, to longer wavelengths 3-12 micrometers for use in gas sensing and sensing of other forms. The underlying principles are much the same except that germanium is typically used in place of silicon in many cases for mid-IR applications, due to the superior transmissivity of germanium at mid-IR wavelengths, and the larger wavelength-to-temperature tuning rate of germanium.

For mid IR range use (roughly 2 to 5 microns wavelength), the tunable filter 104 is made of thin films of germanium and silicon monoxide deposited on a Silicon On Insulator (SOI) wafer. The thin film filter as such is designed and fabricated using well-known methods. For example, in one embodiment, the tunable optical filter 104 is designed with a thin film structure of three resonant cavities, approximately 20 layers, and displays a 'square' transmission region that is about 0.1 micron wide (100 nm) at 4.55 microns wavelength, within which the filter 104 is about 90% transmissive. This particular number of cavities, number of layers, and set of dimensions is only an exemplary case for the purposes of this description, and other constructions may also be used.

Figure 11:
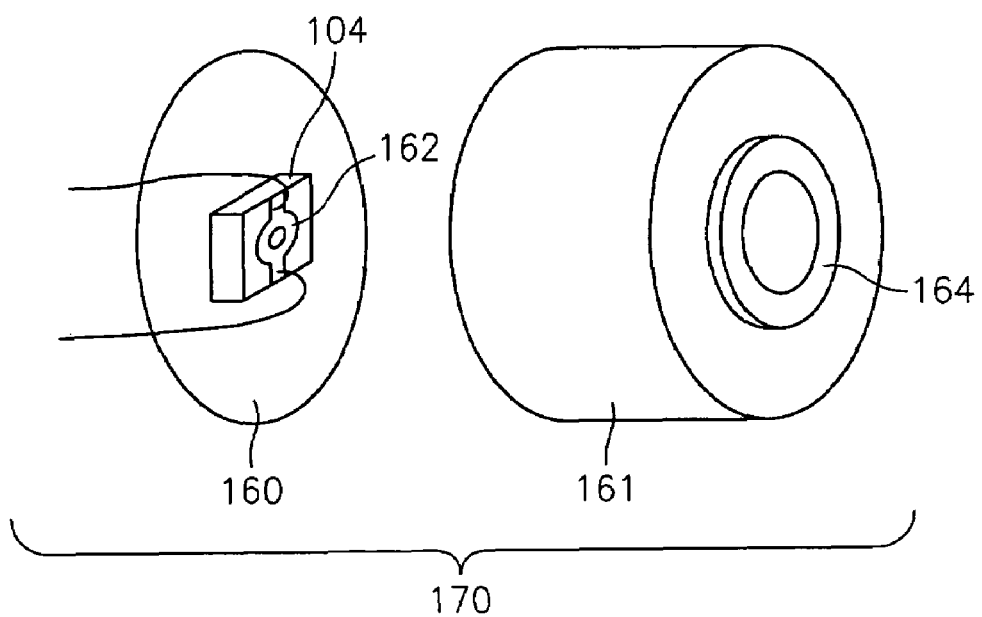
FIG. 11 and FIG. 12 depict aspects of components for the thermally tunable optical sensor.
Figure 12:
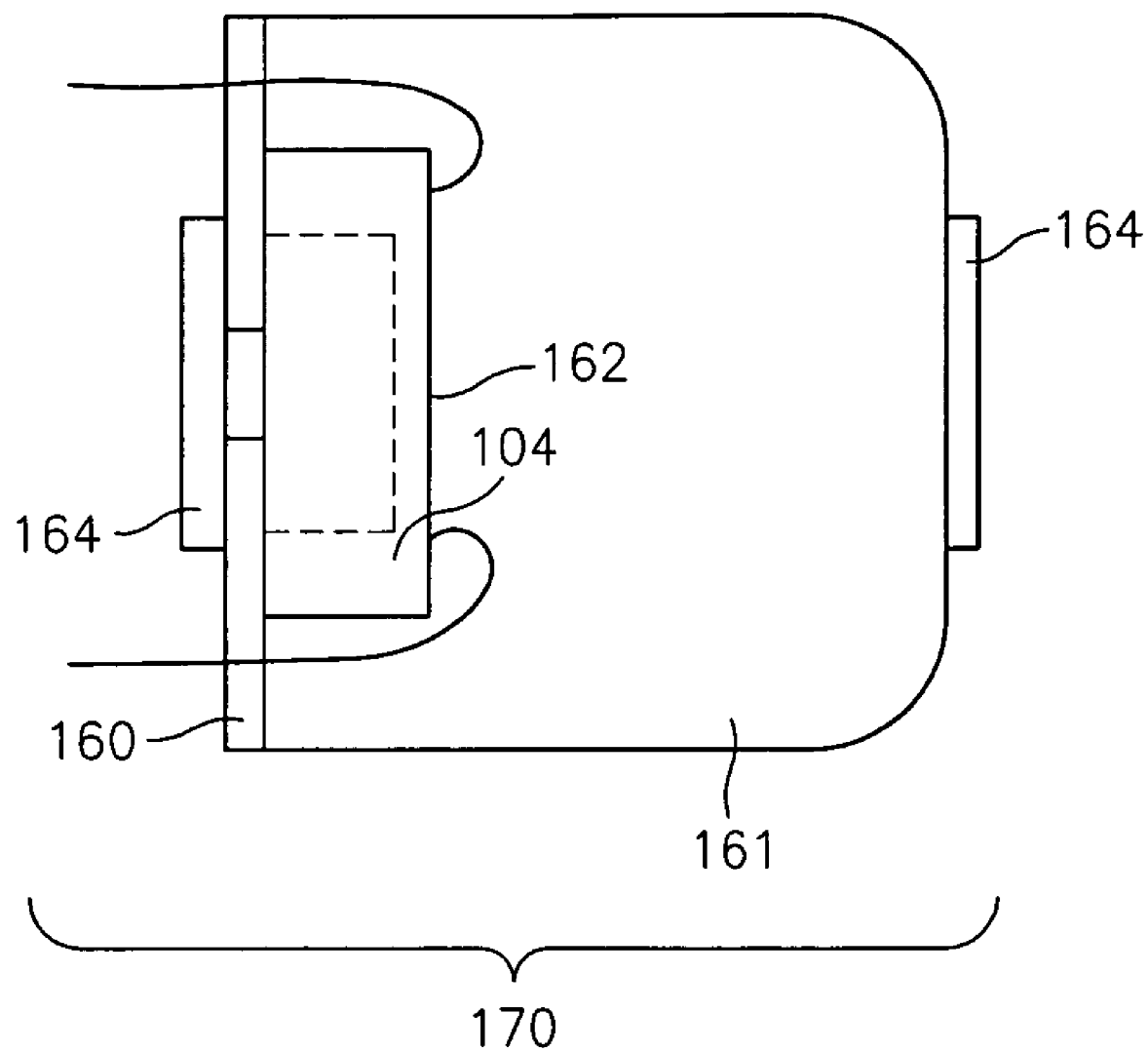

Referring now to FIG. 11 and FIG. 12, an embodiment of the tunable optical filter 104 includes a small container, commonly referred to as a "TO8" can package 170 is shown. The tunable optical filter 104 is mounted on a header 160, which functions as the base of the can package 170. Wire bonds connect the heater ring 162 on the tunable optical filter 104 to pins in the header 130. Blocking filters 144 on the top of the can 161 and on the header 160 allow light within only a bandwidth from about 4000 nm to about 5000 nm to pass, thereby excluding extraneous out-of-band light.

The tunable optical filter 104 is tuned by varying its temperature. In an illustrative case of a germanium-based filter with center wavelength of 4.45 microns, a coefficient of change of center wavelength with temperature is about 0.6 nm per ° C., or 60 nm for each 100° C. The CO absorption band has a double peak structure from about 4420 nm to about 4900 nm. Sensing takes place by tuning the tunable optical filter 104 over the slope that exists near the CO absorption peak from about 4450 nm to about 4570 nm, the tuning range being about 120 nm. This tuning range implies temperature tuning of the filter over a temperature range of about 200° C. Other selections of wavelength variations may be used for particular applications (i.e., detecting other chemicals) or to solve particular problems. For example, a $CO_2$ absorption characteristic occurs just on the short wavelength side of the CO absorption peak, so tuning between two slightly higher wavelengths may avoid interference from $CO_2$ absorption.

Although the described embodiments for the thermally tunable optical sensor 300 use a tunable emitter 102 to provide spectral variation for detecting a chemical absorption peak, other embodiments using alternative configurations may also be used. Various embodiments of an optical chemical sensor are now shown in FIGS. 13A through 13F.

Figure 13A:
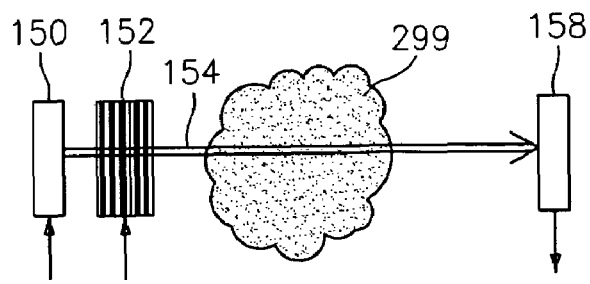
FIG. 13A through FIG. 13F, collectively referred to as FIG. 13, depicts various embodiments of the thermally tunable optical sensor used in the sampling tool; and, FIG. 14 depicts aspects of an exemplary procedure for providing spectroscopy data.

The embodiment in FIG. 13A depicts an adjustment in the location of the tunable optical filter 104 with respect to the emitter 102. The black body radiation source 150 (the emitter 102) produces broad-spectrum (i.e., broadband) IR radiation. A thermo-optically tunable thin film filter 152 (the tunable optical filter 104) is placed in front of this source 150 and associated circuitry scans the filter 152 to various wavelength settings. The filtered radiation 154 passes through the sample chamber 301 containing the sample 299 to be measured, and a broadband detector 158 measures radiation intensity after the radiation passes through the sample 299. The associated circuitry measures for attenuation (a "dip") in the radiation intensity with respect to wavelength to determine whether a particular chemical is present in the sample 299, and if so, the chemical concentration from the magnitude of the dip. The filter 152 and the source 150 are not thermally coupled, so the tunable filter 152 includes a heating element for varying the temperature of the filter 152 independent of the source 150. In one embodiment, the heating element includes a thin film metallic ring deposited on the filter 152.

Figure 13B:
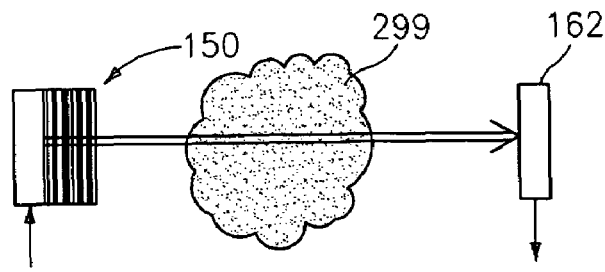

FIG. 13B depicts the configuration of FIG. 7, with the emitter 150 bonded to the filter 152.

Figure 13C:
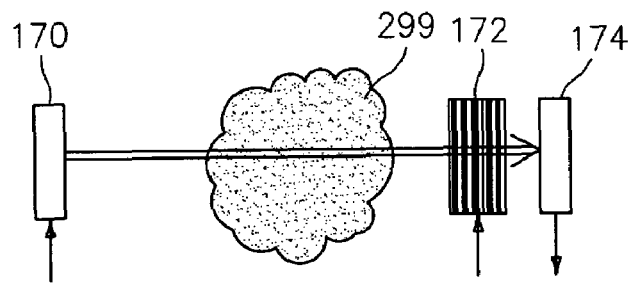

The embodiment shown in FIG. 13C differs from the embodiment in FIG. 7 in that the tunable filter 172 is located near the detector 162. A blackbody radiation source 170 produces broad-spectrum IR radiation. The broadband radiation passes through the sample chamber 301 containing the sample 299, and associated circuitry (not shown) scans a thermo-optically tunable thin film filter 172 to admit different wavelengths of the broadband radiation to a broadband detector 174. The broadband detector 174 measures radiation intensity of the filtered IR radiation from the filter 172. Associated circuitry measures for the "dip" in the radiation intensity with respect to its wavelength to determine whether a particular chemical is present in the sample 299, and if so, the chemical concentration from the magnitude of the dip.

Figure 13D:
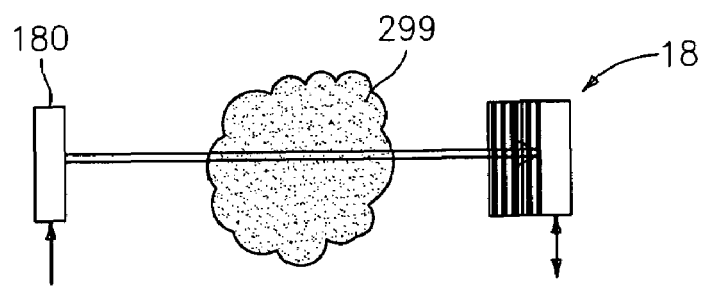

The embodiment shown in FIG. 13D couples the tunable filter and the detector together to form a tunable optical detector (TOD). This embodiment uses a black body radiation source 180 to produce broad-spectrum IR radiation. The broadband radiation passes through the sample chamber 301 containing the sample 299. After passing through the sample 299, a combination of a thermo-optic tunable thin film filter and broadband thermal detector 182 receives the broadband radiation. Associated circuitry (not shown) heats filter/detector 182 to scan different wavelengths, while recording the amount of power required to heat the filter/detector 182 to the corresponding temperatures. When less IR radiation reaches the filter/detector 182 (i.e., when the sample 299 absorbs a portion of the IR light), more energy is required to change temperature (and hence the wavelength) of the filter/detector 182. The external circuitry uses this energy differential to calculate the chemical concentration of the sample 299.

The TOD configuration is useful if the filter, which by virtue of its tuning mechanism must be heated, does not itself radiate so much blackbody radiation as to overwhelm the nearby detector. The package containing the TOD components may be filled with a gas such as xenon to improve the response of the thermopile detector.

Figure 13E:
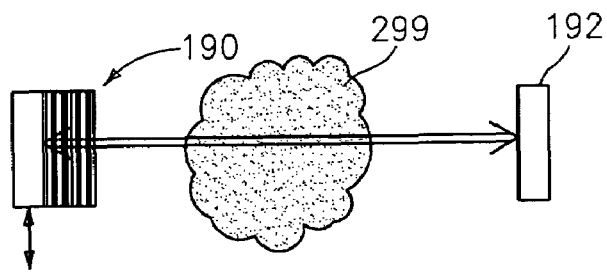

The embodiment of FIG. 13E uses a single combination of a blackbody emitter blackbody detector/thermo-optically tunable filter 190. The combination is heated to emit wavelength-scanning passband infrared radiation. This radiation passes twice through the sample chamber 301 containing the sample 299 with the aid of a retro-reflector 192. The back-reflected radiation is filtered and absorbed in the blackbody emitter/detector combination 190. Similar to the embodiment shown in FIG. 13D, associated circuitry (not shown) heats the combination 190 to scan different wavelengths, while recording the amount of power required to heat the combination 190 to the corresponding temperatures. When less IR radiation reaches the combination 190, more energy is required to change temperature (and hence the wavelength) of the combination 190. The external circuitry uses this energy differential to calculate the chemical concentration in the sample 299.

Figure 13F:
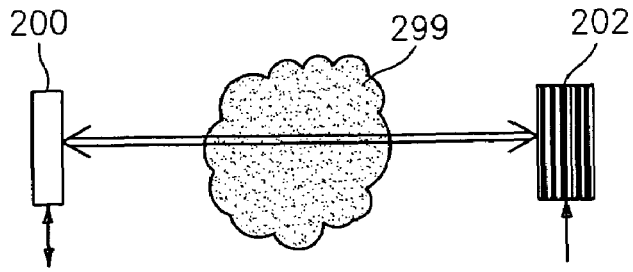

The embodiment of FIG. 13F uses a combined blackbody emitter/detector 200 to produce broadband IR radiation that passes through the sample chamber 301 containing the sample 299. A thermo-optically tunable thin film filter 202 reflects a passband portion of this IR radiation. Associated circuitry (not shown) scans the filter 202 in wavelength. The blackbody emitter/detector 200 reabsorbs the reflected passband portion of the IR radiation after the radiation passes back through the sample 299. Similar to the embodiment shown in FIGS. 13D, associated circuitry (not shown) heats the emitter/detector 200 to scan different wavelengths, while recording the amount of power required to heat the emitter/detector 200 to the corresponding temperatures. When less IR radiation reaches the emitter/detector 200, more energy is required to change temperature (and hence the wavelength) of the emitter/detector 200. The external circuitry uses this energy differential to calculate the chemical concentration in the sample.

In general, the embodiments described in FIG. 13A through FIG. 13F are closely interrelated, with the different types of emitters and detectors in use at different wavelengths. At mid IR wavelengths, low cost emitters include blackbody hot sources (e.g., hot wires and conductive membranes) and low cost detectors include uncooled thermopiles or pyroelectric devices. At near IR wavelengths, low cost emitters include LEDs, and low cost detectors are photon detectors such as PIN photodiodes. At near IR wavelengths, both sources and detectors are much more efficient than those used for mid IR wavelengths.

As a practical matter, these factors restrict the use of a tunable optical detector (FIGS. 13D and 13E) implementation to useful wavelengths in the near IR (less than 2000 nm), where the radiation from the filter heated to about 200° C. to about 300° C., compared to the IR radiation being measured, will not overwhelm the detector. For spectroscopy of (for example) $CO_2$ at the 2000 nm overtone band, or other trace gases with absorptions in the 1400 nm to 1800 nm range, a TOD may be used. At these shorter wavelengths, the typical emitter includes an LED, since a blackbody emitter would require an impractically high temperature to serve as an effective near IR source.

For longer wavelengths, for example 4600 nm, the TOD may be impractical because the hot filter will overwhelm a thermopile detector placed within a few millimeters of separation. In this case, the tunable optical emitter (FIG. 13B) configuration is a better choice.

A tunable optical filter (FIG. 13A and FIG. 13C) configuration, in which the packaged tunable filter is placed in an optical system in such as a way as to be associated with neither emitter nor detector, are also used in alternative embodiments. The embodiments described herein are all based on the tunable filter, whether implemented as TOE, TOD or TOF.

Turning again to the use of the thermally tunable optical sensor 300 for analysis of downhole fluids, one skilled in the art will recognize that the sample chamber 301 may be fabricated to account for high viscosity fluids, or other such aspects of the sample 299. That is, pumping of the sample 299 may provide for extruding a thin film of the fluids. The thin film may be physically separated from the thermally tunable optical sensor 300 by use of highly transmissive materials (e.g., optical quality glass). In some embodiments, the thermally tunable optical sensor 300 is provided in housing that supports immersion into the sample 299, thus providing for greater sensitivity during analysis.

Accordingly, spectral measurements to determine or estimate the mole fraction or percent of chemical groups (aromatics, olefins, saturates) in a crude oil or gas sample using a thermally tunable optical sensor 300 may be realized. Such measurements may be used to determine or estimate or directly measure a gas to oil ratio (GOR) in the formation fluids in a wellbore 11.

The teachings herein further provide for the use of thermally tunable optical sensors 300 in a variety of embodiments. For example, in one embodiment thermally tunable optical sensors 300 are used with the sampling tool 20 to provide real time data. Note that as used herein generation of data in "real-time" is taken to mean generation of data at a rate that is useful or adequate for making decisions during or concurrent with processes such as production, experimentation, verification, and other types of surveys or uses as may be opted for by a user. As a non-limiting example, real-time measurements and calculations may provide users with information necessary to make desired adjustments during the drilling process. In one embodiment, adjustments are enabled on a continuous basis (at the rate of drilling), while in another embodiment, adjustments may require periodic cessation of drilling for assessment of data. Accordingly, it should be recognized that "real-time" is to be taken in context, and does not necessarily indicate the instantaneous determination of data, or make any other suggestions about the temporal frequency of data collection and determination.

In other embodiments, thermally tunable optical sensors 300 are used to provide an analysis of samples 299 remotely retrieved and delivered to the sample chamber 301 of a separate instrument. As an example of these other embodiments, the thermally tunable optical sensors 300 may be employed in a hand tool, field bench equipment, laboratory equipment or as in-line process equipment. More specifically, the present invention is suitable for use in at least one of an exploration setting, a pipeline, a refinery and a laboratory.

A variety of determinations or estimations that may be realized through application of the teachings herein. Spectroscopic data produced in accordance with these teachings may include, without limitation, any one or more of: correlation of spectral measurements to physical properties (API Gravity, cloud point, bubble point, asphaltene precipitation pressure, etc.); chemical properties (acid number, nickel, vanadium, sulfur, mercury, etc.) of crude oil, the ratio, $^{13}C/^{12}C$, of isotopes of methane in natural gas (i.e. not dissolved in a liquid); determinations or estimations phytane/pristane ratios of crude oil; determination or estimation of the $H_2S$ that is dissolved in crude oil (NIR absorbance of 100% $H_2S$ is very weak, so the absorbance of 10 ppm of $H_2S$ is even weaker); estimations as to whether a crude oil sample contains wet gas or dry gas ($C_1$ vs $C_2, C_3, C_4$); determinations or estimations of $CO_2$ in methane gas or of $CO_2$ dissolved in crude oil; determinations or estimations of the ratios, $^{17}O/^{18}O$, of isotopes of water; obtaining "synthetic" course-scale gas chromatograms (the envelope of $C_1, C_2, C_3$ which is the oil's carbon number distribution); determination or estimation of the $^{13}C/^{12}C$ isotopes of methane gas while it is still dissolved in liquid crude oil; determination or estimation of the percentage of oil based mud filtrate contamination in the wellbore 11, particularly if the base oil is aromatic-free (unlike crude oil) but olefin-rich (also unlike crude oil); and, quantification of aromatics, olefins (a chemical class which is unlikely to occur in crude oil but is common in OBM filtrate), saturates, methane, ethane, propane, and butane. Although this is a substantial list of capabilities for the sampling tool 20 equipped with the thermally tunable optical sensor 300, this list is not considered to be exhaustive and is merely illustrative of aspects of the teachings herein.

Further, the teachings herein provide for derivation of a correlative equation from soft modeling such as least mean squares, chemometrics or a neural network to infer physical and chemical properties of sample formation fluids or other fluids, to a degree not previously thought possible by spectroscopy within the wellbore 11. These teachings take advantage of the capability to rapidly perform high resolution spectroscopy or wavelength modulation spectroscopy to find spectral peaks on a shoulder of another peak or to greatly improve signal to noise and makes it possible to observe subtle changes (e.g., 10-20 parts per million (ppm) $H_2S$—not previously possible when performing spectroscopy within the wellbore 11) with lower resolution conventional mid infrared (MIR) and near infrared (NIR) spectroscopy. To improve sensitivity and permit detection of trace amounts of a weakly-absorbing gas, wavelength-modulation spectroscopy can be utilized as described in Equations 1 through 9 of U.S. Patent Application 20050099618, and incorporated herein in its entirety in the Cross Reference above.

Further, the teachings herein provide for resolving the extremely subtle spectral differences between $^{13}C$ methane gas from $^{12}C$ methane gas (provided that the pressure is not so high as to cause excessive pressure-broadening of these peaks to the point that they merge).

Due to the high operating temperatures of the thermally tunable optical sensor 300, it is anticipated that ambient temperature within the wellbore 11 will not be problematic. However, in some embodiments, the sampling tool 20 includes sorption cooling or another cooling mechanism to overcome any temperature issues of operating in a high temperature environment. Typically, for sorption cooling, the thermally tunable optical sensor 300 is placed in thermal contact with a source of water (either liquid or as hydrate). The thermally tunable optical sensor 300 is cooled as the water is evaporated from liquid or released by hydrate. The resulting water vapor is sorbed by a sorbent, which becomes hotter in the process. The sorbent transfers its excess heat to the well bore fluid with which it is in thermal contact through the housing of the sampling tool 20.

Further, the sampling tool 20 fabricated in accordance with the teachings herein is well adapted for harsh environments as the thermally tunable optical sensors 300 are physically robust. That is, the thermally tunable optical sensors 300 are comparatively insensitive to vibration and other aspects of downhole surveillance to which some prior art systems are susceptible.

Figure 14:
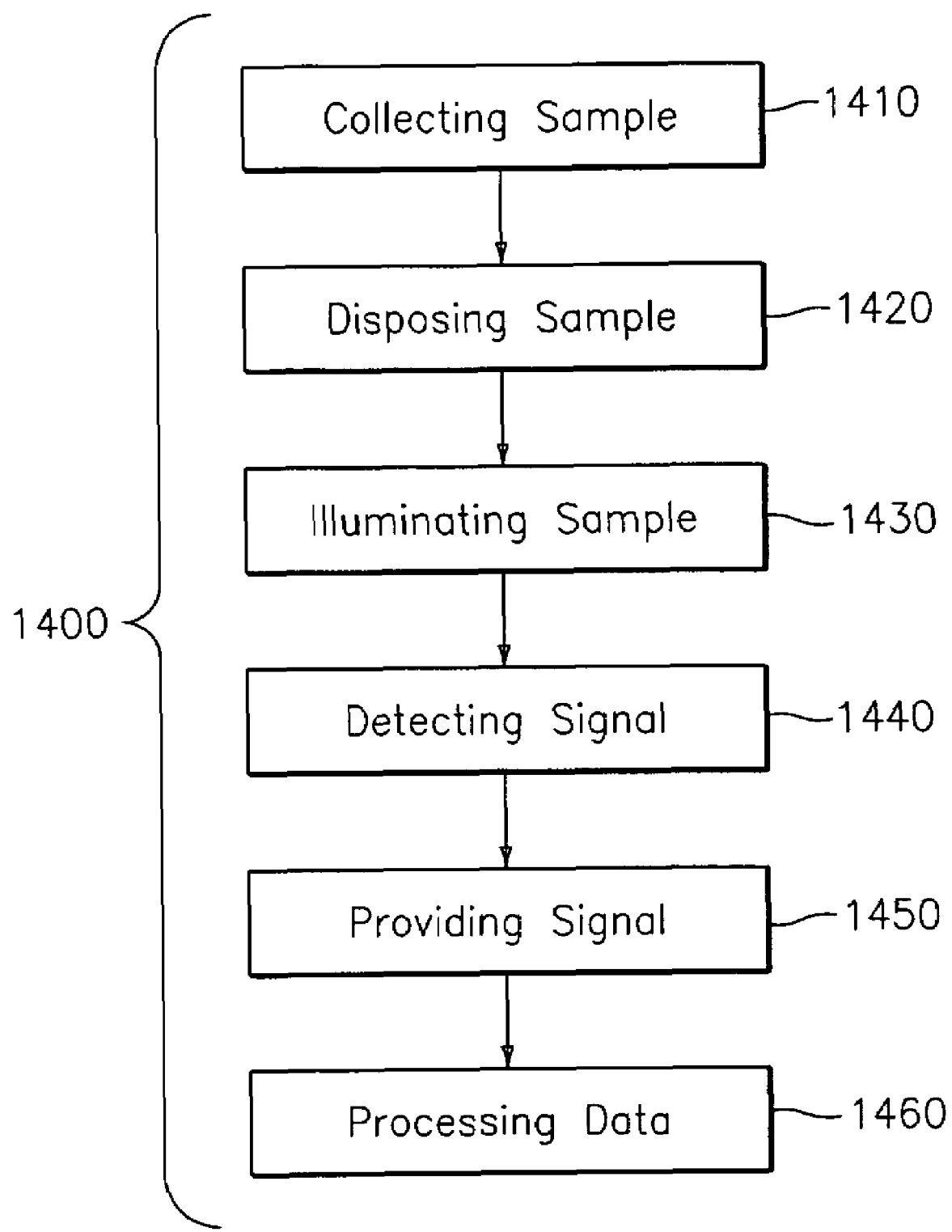

FIG. 14 depicts aspects of an exemplary spectroscopy procedure 1400. In FIG. 14, providing spectroscopic data for the sample 299 taken from the wellbore 11 calls for collecting the sample 1410, disposing at least a portion of the sample 1420 in the sample chamber 301, illuminating the sample 1430 with the series of passbands of emissions of wavelengths; detecting the series 1440 with a detector to produce a detection signal; providing the detection signal 1450 to a processor; and processing 1460 the detection signal to provide the spectroscopy data.

In support of the teachings herein, various computer components including software may be had to provide for operation and analyses of the spectroscopy apparatus and methods disclosed herein. Accordingly, it is considered that these teachings may be implemented as a set computer executable of instructions stored on a computer readable medium, comprising ROM, RAM, CD ROM, flash or any other computer readable medium, now known or unknown that when executed cause a computer to implement the method of the present invention. These instructions may provide for equipment operation, control, data collection and analysis and other functions deemed relevant by a user.

Multi-billion dollar decisions on how to develop a reservoir (well locations, types of production facilities, etc.) are based on a variety of factors, such as whether or not a reservoir is compartmentalized. While a membrane can be used to separate gas from liquid to perform gas isotopic ratio analysis, it is also possible to assess compartmentalization using analysis of phytane/pristane ratios of liquid crude oil or by using any other distinguishing features such as any unexpected subtle differences in the fluid spectra that are capable of being resolved using a sampling tool 20 having capabilities for performing high resolution spectroscopy. Accordingly, the teachings herein provide for a sampling tool 20 that provides the desired capabilities.

While the foregoing disclosure is directed to the exemplary embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

What is claimed is:

1. An apparatus for providing spectroscopic data for a sample, the apparatus comprising:
    a downhole tool that comprises a thermally tunable optical filter for filtering light traversing the sample to provide the spectroscopic data.

2. The apparatus as in claim 1, further comprising:
    an emitter for producing broadband light which travels along a light path that passes through a sample chamber that receives the sample; and
    a detector for receiving light that passes through the sample and for producing a detection signal corresponding to the light the detector receives, wherein the detector and the thermally tunable optical filter are disposed in the light path.

3. The apparatus as in claim 2, further comprising a reflector for concentrating the broadband light produced by the emitter.

4. The apparatus as in claim 2, wherein the emitter generates a series of passband emissions within an operating range.

5. The apparatus as in claim 4, wherein the operating range is centered about an absorption band for a constituent of interest in the sample.

6. The apparatus as in claim 1, wherein the spectroscopic data comprises at least one of:
    a correlation of spectral measurements to one of physical properties and chemical identity; at least one of a ratio of isotopes and a quantity of isotopes; at least one of a determination and an estimation of phytane to pristane ratios; at least one of a determination and an estimation of a dissolved $H_2S$ quantity; a synthetic course-scale gas chromatogram; at least one of a determination and an estimation of a percentage of oil based mud filtrate contamination; and, quantification of at least one of aromatics, olefins, saturates, methane, ethane, propane, and butane in the sample.

7. The apparatus as in claim 1, wherein the sample comprises a mixture of water, drilling fluid and formation fluid.

8. The apparatus as in claim 1, wherein the sample chamber is comprised within in-line process equipment.

9. A method for providing spectroscopic data downhole for a sample, the method comprising:
    illuminating the sample with a series of passbands of wavelength emissions using a thermally tunable optical filter;
    detecting the series emissions that pass through the sample; and,
    processing the detected emissions to provide the spectroscopic data.

10. The method as in claim 9, wherein illuminating comprises:
    producing light having a first wavelength spectrum; and,
    selectively filtering the spectrum to produce filtered light comprising the series of passbands of wavelength emissions.

11. The method as in claim 9, wherein illuminating comprises microtuning the series of passbands of wavelength emissions over an operating range.

12. The method as in claim 11, wherein the operating range at least partially correlates to an absorption band of a constituent of interest in the sample.

13. The method as in claim 9, wherein providing spectroscopic data comprises using a sampling tool to provide the spectroscopic data.

14. The method as in claim 9, wherein providing spectroscopic data comprises using in-line process equipment.

15. The method as in claim 9, wherein providing the spectroscopic data comprises at least one of:
    correlating spectral measurements to physical properties; determining a chemical identity; determining at least one of a ratio of isotopes and a quantity of isotopes; at least one of determining and estimating phytane to pristane ratios; at least one of determining and estimating a dissolved $H_2S$ component; providing a synthetic course-scale gas chromatogram; at least one of determining and estimating a percentage of oil based mud filtrate contamination; and, quantifying at least one of aromatics, olefins, saturates, methane, ethane, propane, and butane in the sample.

16. The method as in claim 9, wherein the sample comprises a mixture of water, drilling fluid and formation fluid.

17. A computer program product stored on machine readable media and comprising instructions for providing spectroscopic data downhole for a sample, the instructions for:

illuminating the sample with a series of passbands of wavelength emissions using a thermally tunable optical filter;

detecting the series emissions that pass through the sample; and, processing the detected emissions to provide the spectroscopic data.

18. The method as in claim 9, wherein producing filtered light comprises:

varying a temperature of the tunable optical filter to produce the series of passbands of wavelength emissions.

* * * * *